United States Patent [19]

Ryan

[11] 4,160,644
[45] Jul. 10, 1979

[54] PLATELET REFERENCE CONTROL AND METHOD OF PREPARATION

[75] Inventor: Wayne L. Ryan, Omaha, Nebr.

[73] Assignee: Streck Laboratories, Inc., Omaha, Nebr.

[21] Appl. No.: 805,810

[22] Filed: Jun. 13, 1977

[51] Int. Cl.² ............................................. G01N 33/16
[52] U.S. Cl. ................................. 23/230 B; 252/408; 424/3
[58] Field of Search ...................... 23/230 B; 252/408; 424/3

[56] References Cited

U.S. PATENT DOCUMENTS

| | | | |
|---|---|---|---|
| 3,574,137 | 4/1971 | Decasperis | 23/230 B |
| 3,632,735 | 1/1972 | Kita | 424/3 |
| 3,634,581 | 1/1972 | Thomas | 424/3 |
| 3,640,896 | 2/1972 | De Casperis | 23/230 B |
| 3,714,345 | 1/1973 | Hirata | 424/3 |
| 3,873,467 | 3/1975 | Hunt | 252/408 |
| 3,884,579 | 5/1975 | Mauthner | 252/408 |
| 3,962,125 | 6/1976 | Armstrong | 23/230BX |
| 3,984,532 | 10/1976 | de Castro | 23/230 B |

OTHER PUBLICATIONS

Preparation of Concentrated Platelet Suspensions by Dehydration Against Polyethyleneglycol 20,000; Akkerman et al. Scand. J. Haematol. (1976) 17, 71–77.

Aggregation of Human Red Blood Cells (RBC) and Platelets and Its Reversal by a Surface-active Substance. Benner et al; Bibliothica Anatomica, No. 12, pp. 208–212 (1973).

Evaluation of Platelet Cryopreservation Techniques by Isolated Kidney Perfusion, Raymond et al., Transfusion, vol. 15, No. 3 1975 pp. 219–225.

*Primary Examiner*—Morris O. Wolk
*Assistant Examiner*—Michael S. Marcus
*Attorney, Agent, or Firm*—Tilton, Fallon, Lungmus & Chestnut

[57] ABSTRACT

A platelet reference control and method of preparation in which a minor amount of solid polyethylene glycol is added either to the platelet suspension or the diluent for the platelet suspension whereby time and agitation stabilization are both achieved.

5 Claims, 2 Drawing Figures

PLATELET REFERENCE CONTROL AND METHOD OF PREPARATION

BACKGROUND AND SUMMARY OF INVENTION

The development of automated counters for counting red blood cells, white blood cells and platelets, together with the increased demand for quality control in the clinical laboratory, produced a need for stabilized cellular components of blood to assess the reproducibility and accuracy of counters. A large number of compounds have been employed to increase the rigidity of the cell membrane of these cellular components so that the cells do not lyse on aging. Examples of these agents: formaldehyde, tannic acid, glutaraldehyde, and pyruvic aldehyde have been used for this purpose.

Platelet reference controls are commercially available from both human and equine platelets. The platelets are removed from the blood by centrifugation, washed with buffered saline and then "fixed" with glutaraldehyde. The final platelet reference control product has a shelf life of at least 6 months at room temperature. The platelet reference control is used in the following manner:

1. It is mixed well to insure uniformity.
2. A micro-pipet is used to remove 5 ul (microliter) of platelets. The 5 ul is placed in 15.0 ml of an isotonic diluent. The exact formula of the diluent differs from company to company, but usually contains sodium chloride, potassium chloride, and a phosphate buffer to maintain the pH at 7.3.
3. The container for the dilution is usually made of polystyrene-disposable plastic with a polyethylene snap-on lid. After adding the platelets to the diluent the container is gently inverted 2-3 times and the platelet mixture is counted. The platelet count under these circumstances is very reproducible ($\pm 2\%$).

However, if the container is agitated vigorously or is allowed to stand for 30 minutes, a decrease in count is observed. For example, counts of 8400-8900 are achieved by gentle inversion while counts of 5600-6700 result from vigorous shaking. Even just setting for 30 minutes will reduce a count from 11,200-11,500 to 10,000-10,100.

The foregoing data is typical of data obtained from samples allowed to set or samples that are vigorously shaken, however, considerable variation of the decrease in platelet count occurs particularly in the samples that are shaken because of the difficulty of calibrating the manner of shaking.

It was postulated that the decrease in platelet counts on shaking or standing was due to adsorption of the platelets on the polystyrene surface. Therefore, glass and silicon coated glass were tested in the same manner as the polystyrene containers and were also found to decrease the platelet counts with time and upon shaking.

Next, an alternative was considered consisting of treatment of the plastic containers with organic solvents such as chloroform, acetone or methylene chloride. This treatment has to be a quick rinse since the solvents, if left in contact with the styrene container, would dissolve it. However, these treatments increased the adsorption of the platelets, viz., a decrease in count.

The increased adsorption following treatment with the solvent suggested that the organic solvent was removing the mold release agent, which is found on the surface of the polystyrene container. Release agents are sprayed on the mold at intervals to assist in obtaining release of the plastic container from the mold. Varying amounts are present on the plastic containers. To pursue this idea further, several mold release agents were sprayed on the interior of the polystyrene-plastic containers used for counting the platelets; the containers were then filled with diluent and platelets and then shook. It was felt that if the release agent were responsible for the variation in counts found from one container to another and for the more rapid decrease in counts after treatment with organic solvents, then, following spraying of the release agent on the container, there should be no decrease in platelet count. It was found that a container once rinsed with trichloro-methane and dried thereafter did not achieve the desired stability, the count dropping from 9900 after gentle inversion to 6300 when shaken vigorously 6 times. However, a mold release agent MS-122 consisting of a fluorocarbon telomer available from Miller-Stephenson Chemical Co., Inc. of Danbury, Conn. produced 10,239 counts after gentle inversion and 10,182 counts after 6 vigorous shakes.

After discussion with several manufacturers of mold release agent, I finally concluded that it might be the surfactant properties of the mold release agents that prevented the adsorption of platelets to the polystyrene surface. For this reason, I examined a variety of cationic, anionic and nonionic surfactants. The cationic surfactants invariably caused aggregation of the platelets. Most of the nonionic and anionic surfactants prevented the decrease in counts that occur on standing or agitation of the platelets. Although the solution to our problem appeared to be at hand, an examination of the size of the surfactant treated platelets in a Coulter ZBI, an instrument which is used for size analysis of particles such as platelets and white blood cells, indicated that there was a large decrease in the size of the platelet. However, when the platelets were examined under the microscope with an ocular-micrometer, no change in size of the platelet could be determined. The principle of the Coulter Counter is that it measures changes in conductivity; the surfactants alter the conductivity and thus make the platelet appear smaller to the instrument. All of the surfactants tested up to this point produced this apparent change in size. The decrease in apparent size is an unacceptable change since most instruments used to count platelets would count them inaccurately under these circumstances.

I thereupon tried a series of polyethylene glycols of which there are several. There is polyethylene glycol 400, polyethylene glycol 4000, polyethylene glycol 6000, polyethylene glycol 20,000. The number following polyethylene glycol is the approximate molecular weight of the polyethylene glycol. Polyethylene glycols are polymers of ethylene oxide with the generalized formula $HOCH_2(CH_2OCH_2)n\ CH_2OH$, n represents the average number of oxyethylene groups. All of the polyethylene glycols decrease surface tension. The liquid polyethylene glycols (200, 300, 400) when added to platelet suspensions did not prevent adsorption of the platelets, that is, a decrease in count still occurs. The PEG-4000, 6000 and 20,000 all were effective in preventing the decrease in counts upon shaking. This was puzzling since the effect on surface tension is similar for all PEG products. Both liquid and solid PEGs in aqueous solutions have surface tensions of about 70 dynes per centimeter at 25° C. at low concentrations and drop to 45–50 dynes/cm at 30–70%.

By the use of a minor amount of solid polyethylene glycol (0.1–0.5 grams) per liter of the platelet reference control dilution, it is possible to stabilize the control against count decrease on either standing or vigorous agitation and without apparent decrease in size which would result in a false low count in instrument counters.

Following the discovery that the minor amounts of polyethylene glycol would stabilize the platelet reference control a search of the art was undertaken to determine how polyethylene glycols had been used previously in conjunction with blood generally and platelets in particular. The search revealed the use of surface active substances such as "Pluronics". These are poly (oxypropylene) poly (oxyethylene) condensates with molecular weights in the range 1,000–15,000 and are produced by BASF Wyandotte. The use of these was reported in *Bibliothica Anatomica*, No. 12, pages 208–212 (1973). Although the addition of the Pluronics to the platelet reference controls prevented aggregation or freezing and adsorption to the container, however, within 10 minutes after addition of the Pluronic to the platelets, the apparent shape started to decrease. It was surprising since the close relationship of Pluronics and polyethylene glycol suggested that the Pluronics might also be satisfactory.

Another prior art reference uncovered in the search also had to do with Cryopreservation Techniques, Transfusion May-June, 1975, Volume 15, No. 3, pages 219–225. This also had to do with the use of additives to platelets for freezing purposes and indicated that dimethyl sulfoxide (DMSO) and polyethylene glycol (PEG) would be useful with the DMSO being superior. However, the DMSO failed to stabilize the platelets.

DETAILED DESCRIPTION

Figure 1:
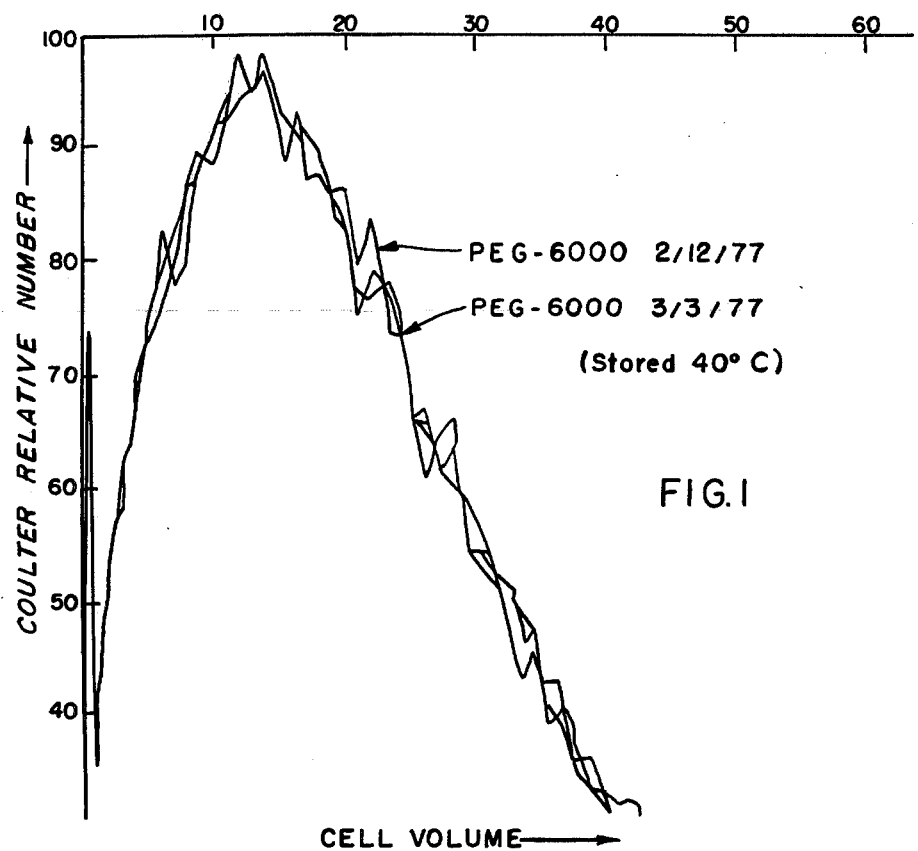
Figure 2:
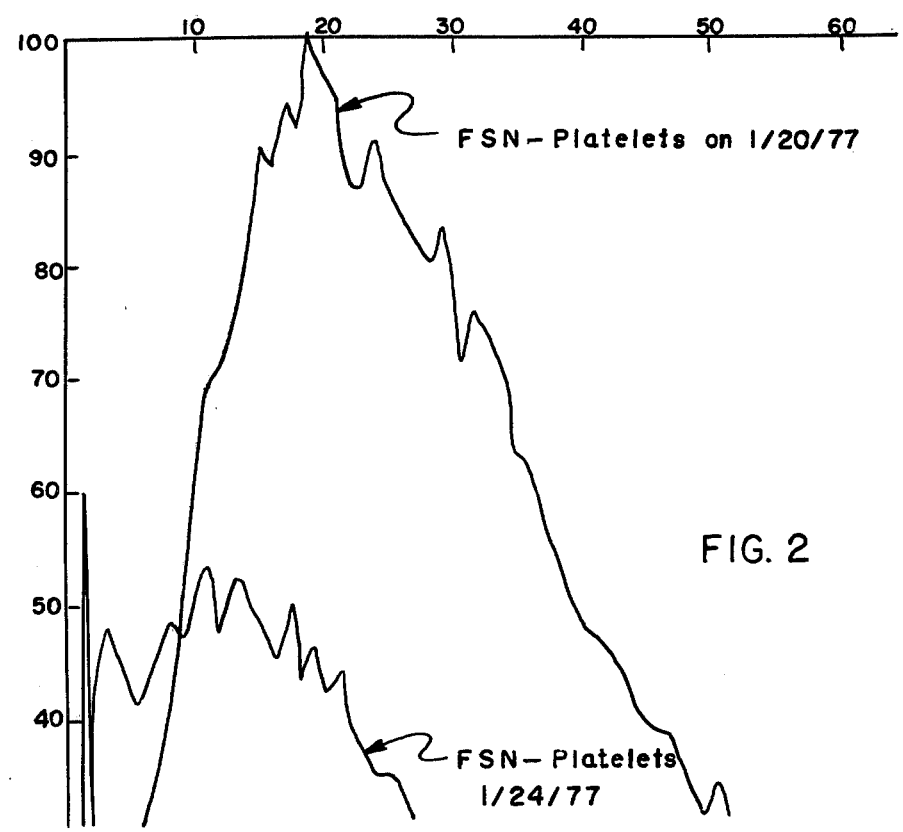

The invention is described in conjunction with the accompanying drawing in which:

FIG. 1 represents two Coulter scans of platelets fortified with PEG-6000 approximately three weeks apart; and FIG. 2 represents two Coulter scans of platelets fortified with a commercial surfactant approximately four days apart.

A typical formulation according to the invention where the solid PEG is added to the platelet suspension includes the following for 100 ml of platelet suspension:
2.0 ml of 25% glutaraldehyde
1.5 grams of $Na_2HPO_4$
10–20 grams of PEG 6000 or PEG 4000

The pH is adjusted to 7.4 and 3.3 ul of the platelet suspension was added to 20 ml of diluent and counted. This formulation was shaken vigorously without any change in platelet count. The same results were obtained when 6.6 ul were added to 20 ml of diluent.

Alternatively, the PEG was added directly to the diluent, according to the following formulation:
0.3 g per liter potassium chloride
7.8 g per liter sodium chloride
2.4 g per liter dibasic sodium phosphate (pH 7.4)
0.1–0.5 g per liter of PEG 4000 or PEG-6000
Platelets added to this diluent do not adsorb, nor is there any decrease in count upon standing in containers. Most important, if the PEG-600 is added to the platelets in the previously mentioned formulation, there is no decrease in apparent size of the platelets. Shown in FIG. 1 is the scan of platelets in PEG-6000 initially, and after 3 weeks at 40° showing the lack of alteration in apparent shape.

Further, the invention can be advantageously practiced with fresh platelets, i.e., those that have not been fixed. Fresh human platelets fortified with solid PEG had a 22.564 count and 22,258 after vigorous shaking. On the other hand, the same platelets without PEG had a count of 22,565 before shaking and a 16,817 count after shaking.

Unacceptable Surfactants

The following surfactants have been tested without the beneficial results of the invention:
Fluorochemical Surfactants FC-128, FC-134, FC-170 Manufactured by the 3M Company
EL-620, EL-719, nonionic surfactants from GAF Corporation, being polyoxylated vegetable oils.
DOW Corning 190 surfactant-a silicone-glycol polymer
DOW Corning 193 surfactant silicon profoamer—aA silicon-polyoxyalkylene copolymer All the following from GAF Corporation, Linden, N.J.
Gafac RP-710: acid ester
Gafac RE-610: acid ester
Gafco LO-529: Partial sodium salt of phosphate ester
Antarox BL-225: Modified linear aliphatic polyether
Antarox BL-240: Modified linear aliphatic polyether
Emulphor EL-620: Polyoxyethylated vegetable oil
Emulphor EL-719: Polyoxyethylated vegetable oil

Dupont Fluorosurfactants

Zonyl FSB—amphoteric
Zonyl FSN—nonionic
Zonyl FSC—cationic
Zonyl FSV—anionic
Zonyl FSP—anionic
Zonyl FSA—anionic All except FSC prevented the decrease in platelet count on shaking. Each surfactant was tested by adding it to the platelet suspension. Platelet suspension (6.6 ul) was then pipeted into 20 ml of saline diluent for cell counting. The amount required to prevent the decrease in platelet count was between 0.1–0.5 ml added to 20 ml of platelet suspension. Of the surfactants, the one which produced the least change in platelet conductivity or "apparent" size was FSN which is nonionic.

An example of the use of FSN in platelet suspension is as follows:

0.1 ml FSN/20 ml of platelet suspension. 6.6 ul of the surfactant-containing platelet suspension was pipeted into 20 ml of diluent. The platelet containing diluent was then counted and the initial count was 9358. After shaking vigorously six times, the count decreased to 7526. 0.5 ml Zonyl FSN/20 ml of platelet suspension was added. Platelet count after gentle inversion was 7622. After shaking for 30 minutes in a polystyrene container, the count was 7670. It is apparent from this that when an appropriate amount of FSN is used the adsorption phenomenon disappears. As a control the non-treated platelet suspension was added (6.6 ul into 20 ml of diluent) count when gently inverted was 10,643, and when shaken vigorously six times, the count decreased to 5,800. The Zonyl preparation used is 50% solids in isopropanol/water. Stability tests were then set up in which 0.5 ml of Zonyl FSN was added to 20 ml of platelet suspension and placed in a sealed container at 40°, 25° and 5° C. The initial tests on the platelets, in addition to counting them, was to measure the size of the platelets on the Coulter ZBI. This was repeated at intervals of 3 days to determine if any changes occurred in either the count, or in the size of the platelets with time. After 3 days, the ZBI indicated that the platelet size had changed. As indicated above, there was not, in fact, a change in the physical dimensions of the platelets as seen under the microscope.

In FIG. 2, the two scans are seen to be quite different and the difference was even more pronounced when using an increased concentration of FSN.

The use of glass and silicon coated glass as mentioned above also did not yield the benefits of the invention as can be seen from the following summary:

| Silicon coated glass | Glass |
| --- | --- |
| 9800 gentle inversion | 10,100 mixed 3 times gently |
| 7780 6 times vigorously | 7,719 shake vigorously 6 times |
| 7300 6 times vigorously | 7,401 shake vigorously 6 times |

While in the foregoing specification, a detailed description of the invention has been set down for the purpose of illustration, many variations in the details hereingiven may be made by those skilled in the art without departing from the spirit and scope of the invention.

I claim:

1. A method of preparing a fixed platelet reference control comprising the steps of stabilizing a fixed platelet reference control against false counts due to container adsorption by adding a solid polyethylene glycol as a stabilizing agent to one member selected from the two member class consisting of an aldehyde fixed platelet suspension member and an isotonic diluent member for a platelet suspension, and thereafter adding the other member to the mixture resulting from the first adding step whereby a control is achieved that is substantially time and agitation stable.

2. The method of claim 1 in which the polyethylene glycol is first added to the suspension and the diluent mixed in thereafter.

3. The method of claim 2 in which about 10–20 grams of polyethylene glycol are added for 100 ml of suspension.

4. The method of claim 1 in which the polyethylene glycol is added to the diluent and the suspension mixed in thereafter.

5. The method of claim 4 in which about 0.1 to about 0.5 grams of polyethylene glycol are added per liter of diluent.

* * * * *